US010857312B2

(12) United States Patent
 Stenzler et al.

(10) Patent No.: US 10,857,312 B2
(45) Date of Patent: Dec. 8, 2020

(54) DUAL RESISTANCE DRY POWDER INHALER

(71) Applicant: Philip Morris Products S.A., Neuchatel (CH)

(72) Inventors: Alex Stenzler, Long Beach, CA (US); Steve Han, Huntington Beach, CA (US); Arthur Slutsky, Toronto (CA); Steven Ellis, Ontario (CA); Noe Zamel, Toronto (CA); William Alston, San Jose, CA (US)

(73) Assignee: Philip Morris Products S.A., Neuchatel (CH)

( * ) Notice: Subject to any disclaimer, the term of this patent is extended or adjusted under 35 U.S.C. 154(b) by 357 days.

(21) Appl. No.: 15/566,351

(22) PCT Filed: Apr. 13, 2016

(86) PCT No.: PCT/US2016/027248
§ 371 (c)(1),
(2) Date: Oct. 13, 2017

(87) PCT Pub. No.: WO2016/168271
PCT Pub. Date: Oct. 20, 2016

(65) Prior Publication Data
US 2018/0093051 A1 Apr. 5, 2018

Related U.S. Application Data

(60) Provisional application No. 62/147,806, filed on Apr. 15, 2015, provisional application No. 62/147,803, filed on Apr. 15, 2015.

(51) Int. Cl.
 *A61M 15/00* (2006.01)
 *A61M 15/06* (2006.01)
 *A61M 11/00* (2006.01)

(52) U.S. Cl.
 CPC ...... *A61M 15/0015* (2014.02); *A61M 11/001* (2014.02); *A61M 15/0021* (2014.02);
 (Continued)

(58) Field of Classification Search
 CPC .. A61M 15/00; A61M 15/06; A61M 15/0013; A61M 15/0015; A61M 15/0016;
 (Continued)

(56) References Cited

U.S. PATENT DOCUMENTS

| 5,441,060 A | 8/1995 | Rose et al. |
| 6,102,036 A | 8/2000 | Slutsky et al. |

(Continued)

FOREIGN PATENT DOCUMENTS

| CN | 101588831 A | 11/2009 |
| CN | 204104840 U | 1/2015 |

(Continued)

OTHER PUBLICATIONS

Supplementary Partial European Search Report for EP 16780605.8, dated Dec. 21, 2018, issued by the European Patent Office; 14 pgs.
(Continued)

*Primary Examiner* — Kendra D Carter
*Assistant Examiner* — Elliot S Ruddie
(74) *Attorney, Agent, or Firm* — Mueting Raasch Group

(57) ABSTRACT

Described is a dry powder inhaler for inhalation of a dry powder composition. The inhaler includes an external housing that defines an internal passage. The inhaler also includes a mouthpiece, a compartment for holding a dry powder capsule or powder reservoir, and a powder fluidization and deagglomeration apparatus for directing airflow to the dry powder to generate airborne powder particles within the internal passage. When a user inhales through the mouthpiece, a first airflow pattern is generated that has a first airflow resistance, during which the fluidization and
(Continued)

deagglomeration apparatus generates airborne dry powder particles within the internal passage. Upon reaching a threshold negative pressure value within the internal passage of the inhaler, a second airflow pattern is generated having a second airflow resistance that is lower than the first airflow resistance, which pulls the airborne dry powder into the user's lungs during the inhalation. Embodiments of elastomeric valves are also described.

14 Claims, 13 Drawing Sheets

(52) U.S. Cl.
CPC .... *A61M 15/0028* (2013.01); *A61M 15/0086* (2013.01); *A61M 15/06* (2013.01); *A61M 2202/064* (2013.01)

(58) Field of Classification Search
CPC .... A61M 15/0018; A61M 15/005–008; A61M 11/001; A61M 15/002; A61M 15/0021; A61M 15/0028–0041; A61M 15/0086; A61M 15/0093; A61M 11/06; A61M 16/14; A61M 16/20; A61M 16/208; A61M 16/209; A61M 2202/064; A61M 2206/01; A61M 15/0001; A61M 15/0005; A61M 15/0066; A61M 15/0091–0096
USPC ............ 128/202.21, 203.12, 203.15, 207.16; 131/273, 338; 604/58
See application file for complete search history.

(56) References Cited

U.S. PATENT DOCUMENTS

| | | | | |
|---|---|---|---|---|
| 6,234,169 | B1* | 5/2001 | Bulbrook | A61M 15/06 128/203.12 |
| 6,606,992 | B1* | 8/2003 | Schuler | A61M 16/0495 128/203.15 |
| 8,215,300 | B2* | 7/2012 | Steiner | A61M 15/0028 128/203.12 |
| 8,261,739 | B2 | 9/2012 | Harris et al. | |
| 2003/0168057 | A1 | 9/2003 | Snyder et al. | |
| 2007/0240712 | A1* | 10/2007 | Fleming | A61M 15/0003 128/203.15 |
| 2010/0247715 | A1 | 9/2010 | Pastor Muntada | |
| 2014/0014106 | A1 | 1/2014 | Smutney et al. | |
| 2017/0368273 | A1* | 12/2017 | Rubin | A61M 11/042 |

FOREIGN PATENT DOCUMENTS

| | | |
|---|---|---|
| EP | 0626180 B1 | 4/1999 |
| JP | H09253209 A | 9/1997 |
| JP | 2002-165884 A | 6/2002 |
| JP | 2002522173 A | 7/2002 |
| WO | WO 00/09188 A1 | 2/2000 |
| WO | WO 2008/051621 A2 | 5/2008 |
| WO | WO 2014/085719 A1 | 6/2014 |

OTHER PUBLICATIONS

International Search Report and Written Opinion for PCT/US16/27248, issued by the U.S. Patent Office as the Search Authority, dated Aug. 25, 2016, 10 pgs.
International Preliminary Report on Patentability for PCT/US216/027248, issued by the International Bureau of WIPO, dated Oct. 17, 2017: 7 pgs.
Japanese Office Action issued for JP Application No. 2018-505570, by the Japanese Patent Office dated Mar. 30, 2020; 11 pgs. including English Translation.
Chinese Office Action issued for CN Application No. 201680032941.0, by the China National Intellectual Property Administration dated Feb. 26, 2020; 11 pgs. including English Translation.
Russian Office Action issued by the Russian Patent Office for RU Application No. 2017136805; dated Aug. 5, 2020; 15 pgs.

* cited by examiner

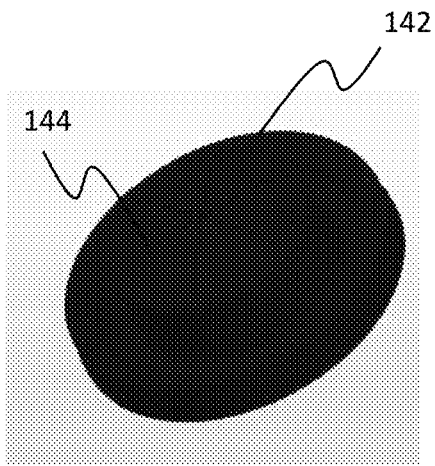
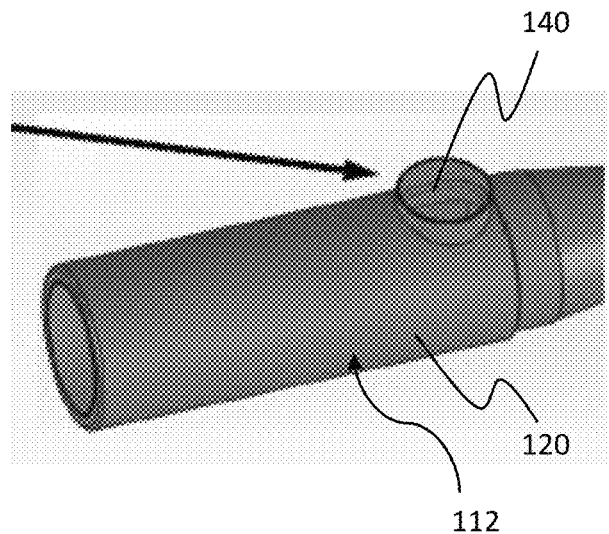
Fig. 6A               Fig. 6B
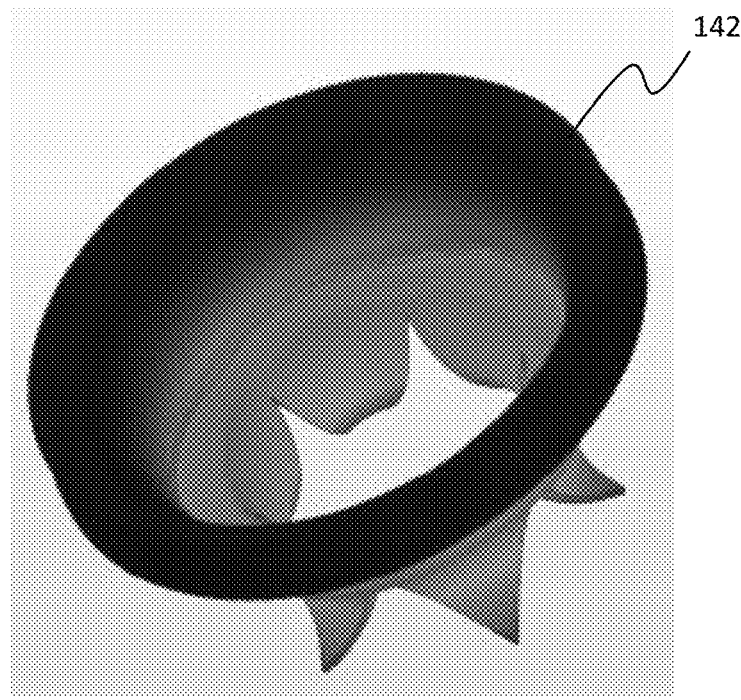
Fig. 6C

Fig. 8A

Fig. 8B

DUAL RESISTANCE DRY POWDER INHALER

CROSS-REFERENCE TO RELATED APPLICATIONS

This application is a national stage entry of PCT/US16/27248, filed on Apr. 13, 2016, which claims priority to U.S. provisional application No. 62/147,806 filed on Apr. 15, 2015, and U.S. provisional application No. 62/147,803 filed on Apr. 15, 2015, all of which are incorporated herein by reference in their entireties.

BACKGROUND OF THE INVENTION

Inhalation of nicotine-based powder formulations has become an effective and popular way to deliver nicotine to the bloodstream while reducing the hazardous effects of smoking, such as those associated with unpleasant odors and second hand smoke. For example, dry powder inhalers allow users to inhale nicotine powder from the device for delivery to the lungs and absorption into the bloodstream. One such device has been described in U.S. Pat. No. 6,234,169 to Bulbrook et al. ("Bulbrook"), herein incorporated by reference in its entirety. Embodiments described by Bulbrook, and other dry powder inhaler designs known in the art, require entrainment of powder in a reservoir for drawing the powder into an air inhalation stream for inhalation by the user.

However, these devices struggle to mimic the routine of smoking a traditional cigarette. Inhalation of cigarette smoke is typically a two-step movement. For example, when smoking a traditional cigarette, a typical inhalation technique first involves taking an initial drag from the cigarette. During this initial drag, the user's lips are sealed around the cigarette while they inhale, producing a negative pressure or "vacuum," pulling the smoke from the cigarette's burning rolled tobacco leaves into the user's mouth. This movement of air against the burning rolled tobacco leaves is a high resistance movement. Because the user wants to get the nicotine-laden smoke to their lungs for absorption into the bloodstream, the user will typically remove the cigarette from their mouth and inhale the smoke into their lungs by opening their mouth and taking a deep breath. Since the cigarette has been removed from the lips, this inhalation provides a low resistance intake of air, allowing for deep delivery of smoke into the lungs. Duplicating this inhalation pattern with existing dry powder inhalers is ineffective, because during the short period of time that the inhaler is removed from the mouth, the majority of powder drawn into the mouth settles, leaving only a fraction of the nicotine-based powder to be drawn deeper into the lungs.

Further, valves are commonly used devices for controlling the flow of fluids, gases and other substances. They are utilized in some shape or form across virtually every industry. Generally, valves can be fully open to allow full access to a pathway, fully closed to restrict all access to a pathway, or partially open/closed to create partial access or partial blockage to a pathway, depending on the particular application of the valve. Some types of valves operate by manual or user actuation, such as by turning a handle, lifting a lever, or squeezing the valve. Other types of valves actuate automatically, such as those that actuate in response to threshold pressures, temperatures or material flow.

There are however a number of drawbacks to conventional pressure actuated elastomeric valve designs. For instance, many pressure actuated elastomeric valves have complex geometries. In a manufacturing setting, the scrap rate of these valves is often higher than desired since high efficiency molding processes for complex valve geometries are often difficult to achieve in a mass production format. Another problem is the lack of aesthetic value in conventional valve designs. In many instances, valves are integrated into systems such that they are not visible to users of the system. When the valve is not visible, or if the application is one that does not require an aesthetic appeal, the aesthetic value of the valve design is insignificant. However, there may be other instances where the valve is visible to the user, and likewise, the aesthetic valve of the visible valve is important for product design. Further, even in instances when the valve is not visible, and aesthetic valve is not important, elastomeric membranes are often seated in such a manner that either adds excess bulk to the device, impedes the flow through the pathway, or both. A more elegant and efficient solution would be of benefit. Still further, conventional elastomeric valves, such as slit valves, are often prone to durability issues, and also are prone to performance issues. For example, the sides surrounding the slit on a slit valve tend to pucker upon closing instead of closing flushly, and a proper seal is not achieved. Other types of conventional pressure actuated elastomeric valves have their own issues. For instance, duckbill valves tend to be more durable, however, in devices where gases are being used to actuate the valve, it may be harder to design a duckbill valve with a reliable opening threshold pressure.

What is needed is a device, system and method for inhaling dry powder nicotine formulations in a manner that mimics the resistance flow pattern for smoking traditional cigarettes. Further, there is a need in the art for a pressure actuated elastomeric valve with a simple geometry that is easy to manufacture. When exposed to a visible surface, the valve should be able to integrate itself with the contours of its associated device, thus maintaining a high aesthetic value for the valve and the device. The seating for the elastomeric membrane should minimize housing bulk and minimize impedance with flow pathways. Further, the design should be provide reliable actuation in response to a pressure generated in an air or gas-like medium. The present invention meets these needs. Additional performance improvements for the pressure actuated elastomeric valve disclosed herein will be apparent.

SUMMARY OF THE INVENTION

A device for inhalation of a dry powder composition is described. In one embodiment, the device includes an external housing having a proximal end, a distal end and a length therebetween, where the housing defines an internal passage having proximal, intermediate and distal regions along the housing length. The device further includes a proximal end opening, a distal end opening and proximal region opening each in connection with the internal passage. Also included in the device is a dry powder compartment within the distal region of the internal passage, and a powder fluidization and deagglomeration apparatus within the intermediate region of the internal passage. When a vacuum is applied to the proximal end opening and the proximal region opening is closed, a first airflow pattern is generated from the distal end opening to the proximal end opening having a first airflow resistance, and when the proximal region opening is open, a second airflow pattern is generated having a second airflow resistance that is lower than the first airflow resistance. In another embodiment, the device includes a valve associated with the proximal region opening. In another embodiment, the valve is configured to open responsive to a threshold negative pressure value within the proximal region of the internal passage. In another embodiment, the valve includes a flexible component attached to only a portion of the proximal region opening perimeter. In another embodiment, the portion of the flexible component detached from the proximal region opening perimeter forms a flap that separates from the proximal region opening perimeter and at least partially recesses into the internal passage when a threshold negative pressure value is reached within the internal passage. In another embodiment, the valve includes a flexible component having at least one slit to form at least one valve flap. In another embodiment, the at least one valve flap at least partially recesses into the internal passage when a threshold negative pressure value is reached within the internal passage. In another embodiment, the valve is a mechanical valve. In another embodiment, the dry powder compartment is a disposable capsule positioned within the distal region of the internal passage. In another embodiment, the dry powder compartment is a reservoir. In another embodiment, the powder fluidization and deagglomeration apparatus is in fluid communication with the dry powder compartment. In another embodiment, the powder fluidization and deagglomeration apparatus is detachable from the device housing. In another embodiment, the powder fluidization and deagglomeration apparatus is integrated with the device housing. In another embodiment, the external housing is substantially cylindrical along its length. In another embodiment, the valve has a profile that is substantially the same as the profile of the external housing adjacent the proximal region opening.

A method for delivering a dry powder composition into the lungs of a user is also described. In one embodiment, the method includes the steps of inserting a dry powder composition into an inhaler, generating a negative pressure within the inhaler via an inhalation by a user to create a first airflow pattern within the inhaler at a first airflow resistance, such that at least a portion of the dry powder composition becomes airborne within the inhaler, and generating a second airflow pattern within the inhaler having a second airflow resistance that is lower than the first airflow resistance, such that the airborne dry powder is pulled by the negative pressure into the user's lungs during the inhalation. In another embodiment, the step of generating the second airflow pattern is automated by the inhaler. In another embodiment, the step of generating the second airflow pattern occurs when a threshold negative pressure value is reached within the inhaler. In another embodiment, the step of generating the second airflow pattern is triggered by a valve opening at the threshold negative pressure value. In another embodiment, the first airflow pattern is at least partially blocked by the generation of the second airflow pattern.

In one embodiment, a pressure actuated valve includes a single panel elastomeric member partially fixed into an opening within the wall of a conduit, such that at least one edge of the elastomeric member is detachable from the conduit wall opening; wherein the single panel elastomeric member has a first, relaxed configuration and a second, flexed configuration, such that the opening within the wall of the conduit is sealed by the single panel elastomeric member in the first configuration, and unsealed along the at least one detachable edge when the single panel elastomeric member is in the second, flexed configuration. In one embodiment, the single panel elastomeric member has a first thickness in a central region along at least a portion of its length and a second thickness in at least a portion of peripheral regions flanking the central region, wherein the second thickness is less than the first thickness. In one embodiment, the single panel elastomeric member is configured to have a substantially bi-stable movement between the first and second configurations in response to a threshold pressure differential. In one embodiment, the single panel elastomeric member has a delayed movement when the threshold pressure differential is reached. In one embodiment, a surface contour of the single panel elastomeric member matches a profile of a surface contour of the conduit sidewall. In one embodiment, the single panel elastomeric member comprises silicone rubber. In one embodiment, the silicone rubber is between 10 and 40 Shore A durometer. In one embodiment, the threshold pressure differential is between 10 and 60 cm $H_2O$. In one embodiment, the elastomeric member at least partially blocks flow within a lumen of the conduit when in the second, flexed configuration.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 2A shows the dry powder inhaler with the valve in a closed state, and FIG. 2B shows the dry powder inhaler with the valve in an open state.

FIG. 3A shows the dry powder inhaler with the valve in a closed state, and FIG. 3B shows the dry powder inhaler with the valve in an open state.

FIGS. 6A and 6C are perspective views of a slit valve according to an aspect of an exemplary embodiment of the invention. FIG. 6A shows the valve in a closed position, and FIG. 6C shows the valve in an open position. FIG. 6B is a perspective view of a valve housing according to an aspect of an exemplary embodiment of the invention.

FIG. 7A is a view of the dry powder inhaler with the valve in a closed state, and FIG. 7B is a view of the dry powder inhaler with the valve in an open state.

FIG. 8A is a graph showing a preferred flow resistance over time, and FIG. 8B is a graph showing a preferred volume flow rate over time, each according to aspects of an exemplary embodiment of the invention.

FIG. 9A shows the valve in a closed configuration, and FIG. 9B shows the valve in an open configuration.

FIG. 10A is a perspective view of the elastomeric member. FIG. 10B is an end view of the elastomeric member. FIG. 10C is a perspective view of both the open state and closed state of the elastomeric member for purposes of illustrating the deflection of the detached edge.

FIG. 11A shows the valve in a closed state. FIG. 11B shows the valve in an open state, partially blocking the lumen. FIG. 11C shows the valve in an open state, fully blocking the lumen.

FIG. 12A shows the valve in a closed configuration, and FIG. 12B shows the valve in an open configuration.

FIG. 13A shows the valve in a closed configuration, and FIG. 13B shows the valve in an open configuration.

DETAILED DESCRIPTION OF THE INVENTION

Figure 1:
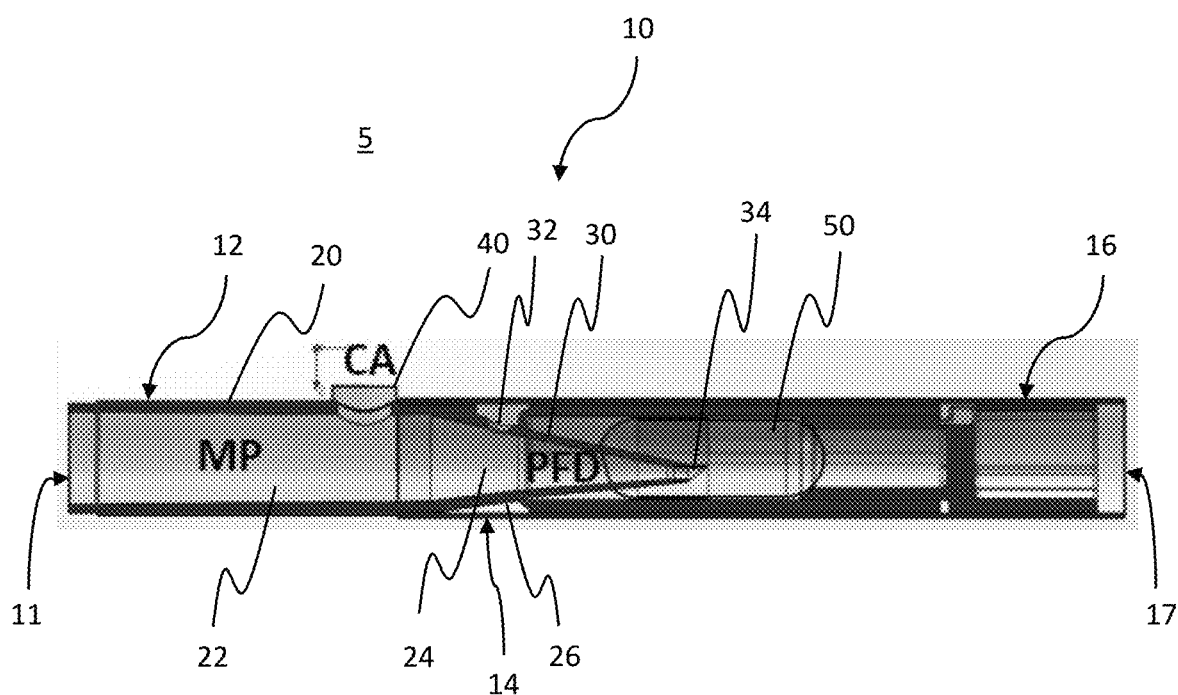
FIG. 1 is a cross-sectional view of a dry powder inhaler according to an exemplary embodiment of the invention.
Figure 2A:
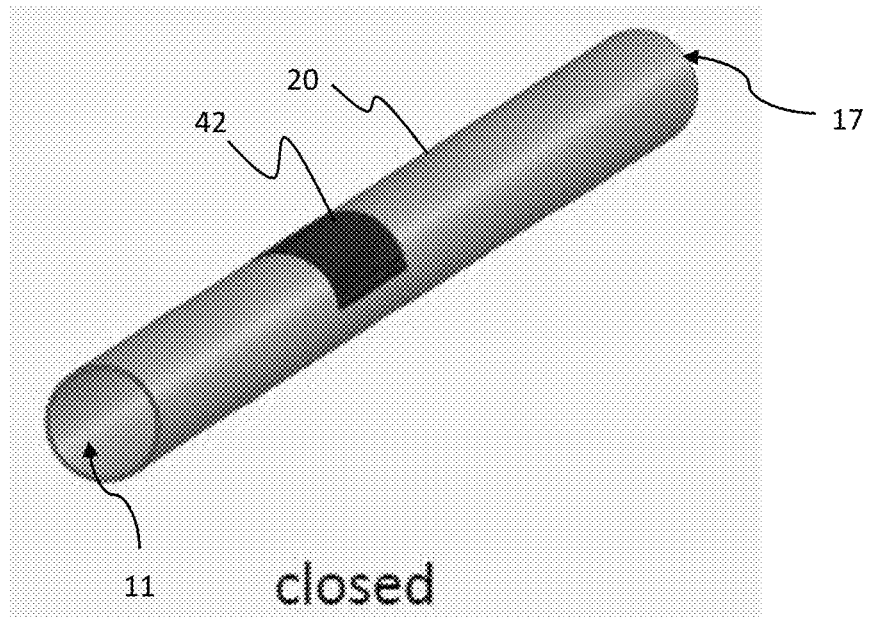
FIGS. 2A and 2B are perspective views of a dry powder inhaler according to an exemplary embodiment of the invention.
Figure 2B:
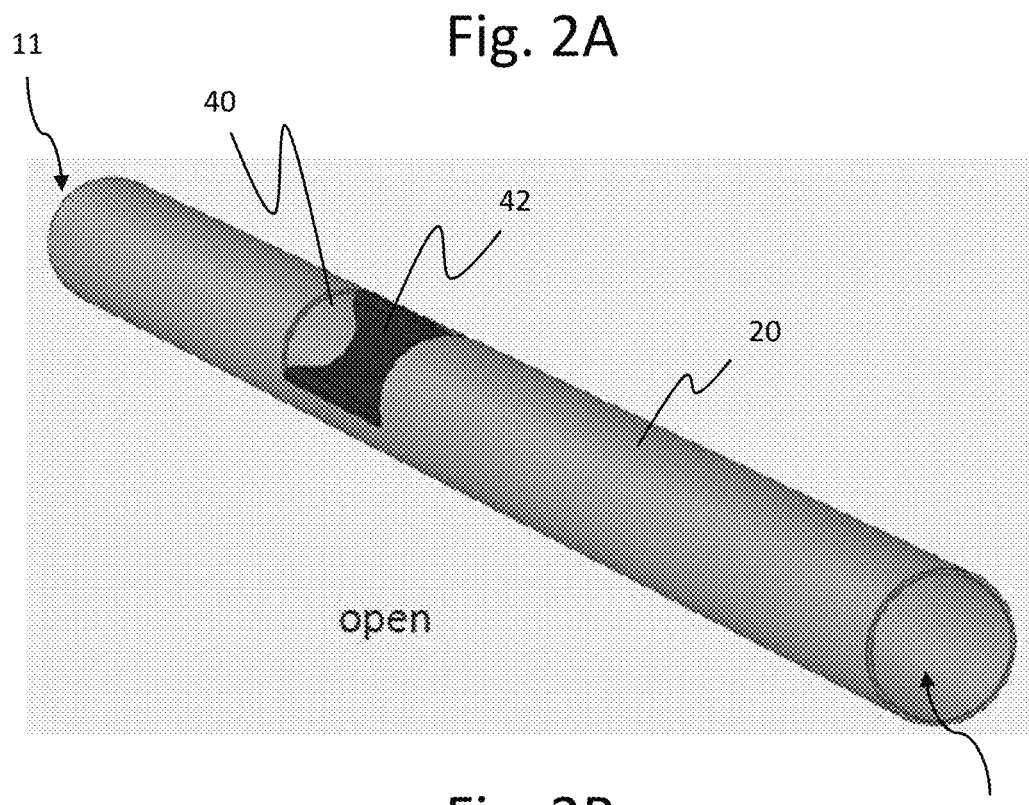
Figure 3A:
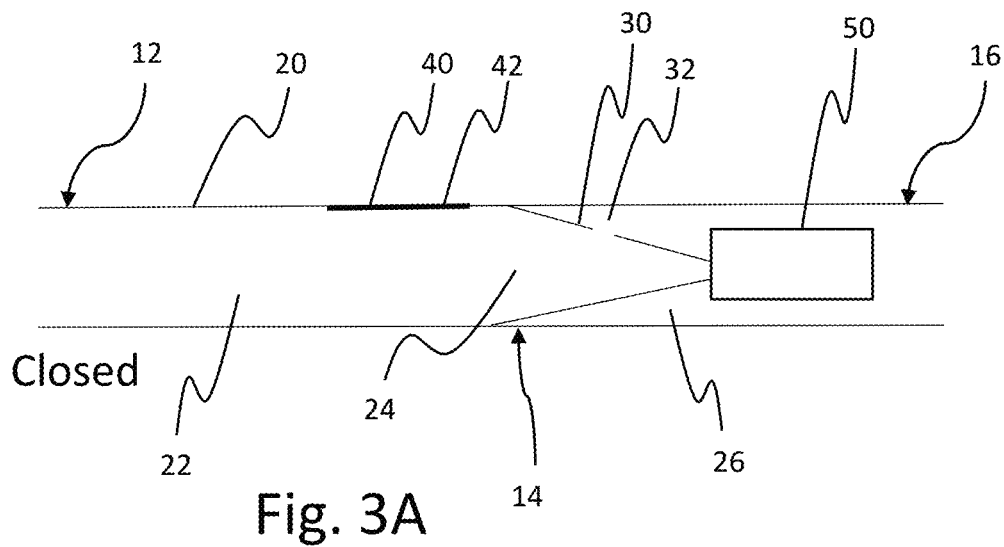
FIGS. 3A and 3B are cross-sectional views of the dry powder inhaler shown in FIGS. 2A and 2B.
Figure 3B:
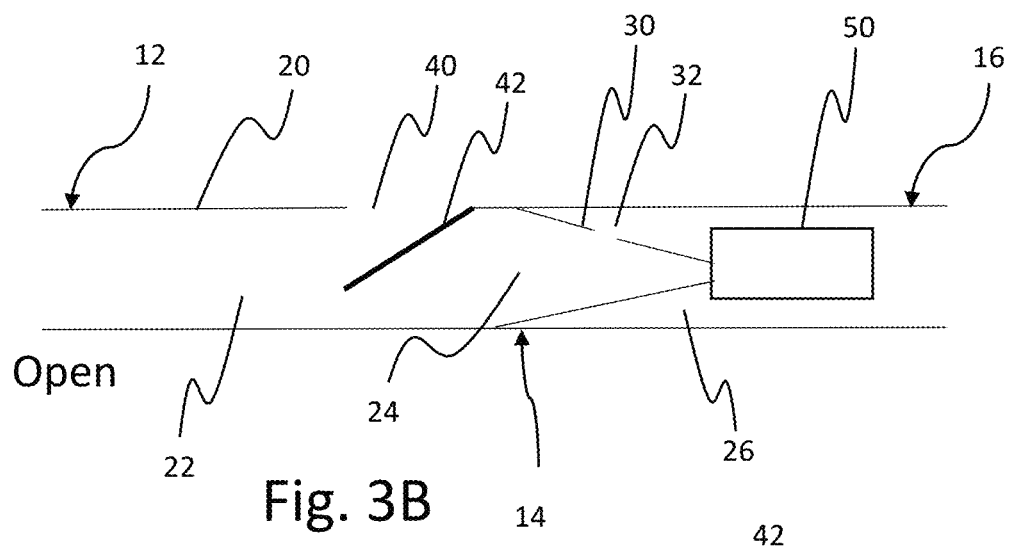
Figure 3C:
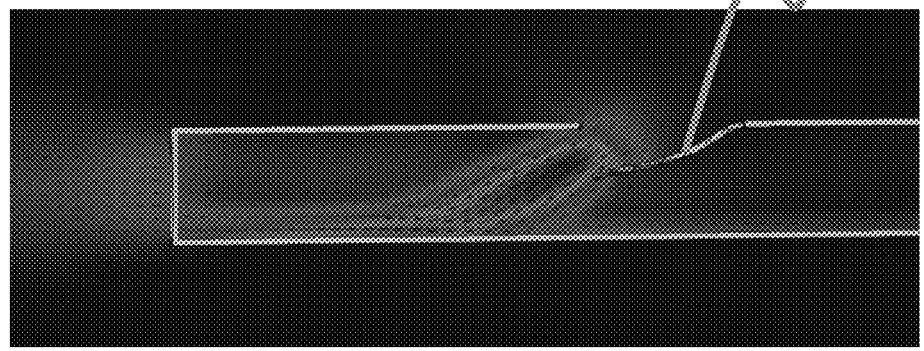
FIG. 3C is an inhalation airflow diagram with the valve in an open state.
Figure 4A:
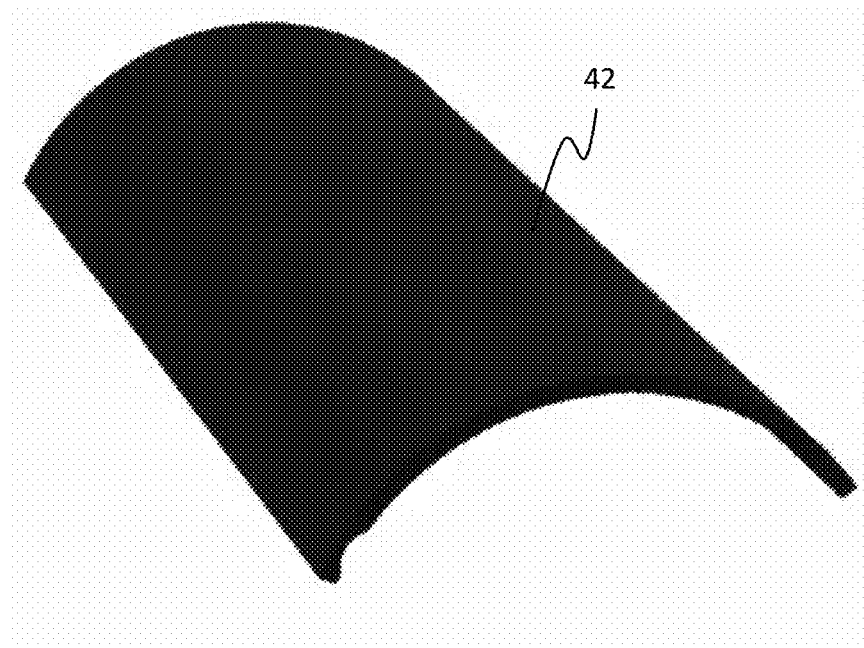
FIGS. 4A and 4B are perspective and end views respectively of the flexible valve element shown on the dry powder inhaler of FIGS. 2A and 2B.
Figure 4B:
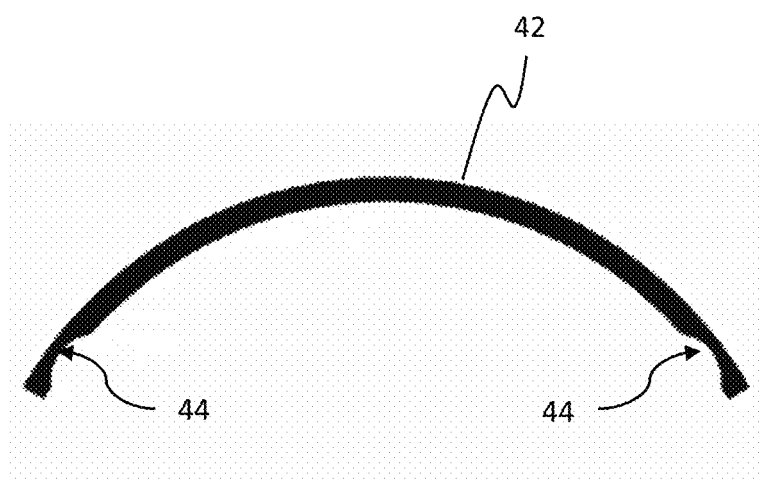

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "dry powder" refers to a fine particulate composition that is not suspended or dissolved in a propellant, carrier, or other liquid, and it is not meant to necessarily imply a complete absence of all water molecules.

Unless stated otherwise, the described size or size range of a particle should be considered as the mass median aerodynamic diameter (MMAD) of the particle or set of particles. Such values are based on the distribution of the aerodynamic particle diameters defined as the diameter of a sphere with a density of 1 gm/cm$^3$ that has the same aerodynamic behavior as the particle which is being characterized. Because the particles described herein may be in a variety of densities and shapes, the size of the particles is expressed as the MMAD and not the actual diameter of the particles.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a dry powder inhaler capable of providing at least two levels of flow resistance, or variable flow resistance, during a single user inhalation.

With reference to FIG. 1, the dry powder inhaler or device 10 is formed from a housing 20 in the form of a shaft extending from a proximal end 12 to a distal end 16. Preferably, the housing 20 may form a generally cylindrical shape, similar to a conventional cigarette. In alternative embodiments, the device housing can form any other desired shape, such as substantially rectangular, triangular, trapezoidal or any other shape, as will be appreciated by those having ordinary skill in the art. The proximal tip of the device 10 has a round opening 11, forming a mouthpiece (MP) that allows a user to inhale through the opening 11 and generate a negative pressure at the proximal end 12 of the device 10. It should be appreciated that opening 11 may be any shape desired, such as oval, or a narrowed slit. Preferably, opening 11 is ergonomically shaped or contoured in conjunction with the proximal end of the MP to fit comfortably within the subject's mouth. An intermediate region 14 of device 10 includes a powder fluidization and deagglomeration apparatus (PFD) positioned within an interior chamber 26 of the device housing 20. The PFD may be integrated with the interior surface of housing 20 as a single unit, or the PFD may be a separate component that is removable from the interior of housing 20. The PFD also has a housing wall 30 forming an internal chamber 24. The PFD further includes an opening 34 at its distal end which may further serve as a piercing component for piercing a container of dry powder, such as dry powder capsule 50. Opening 34 includes a channel into internal chamber 24, such that an air passage is created between the inside of capsule 50 and internal chamber 24 of the PFD. Alternatively, opening 34 of the PFD may be positioned to access a dry powder reservoir within housing 20. As contemplated herein, the PFD housing wall 30 can form a number of geometries defining internal chamber 24, including a tapered geometry forming a frusto-conical chamber 24, as shown in FIG. 1. Functionally, the PFD provides powder fluidization, or entraining powder in the air stream, and for reducing fluidized powder suspended in the air stream to at or near primary particle state. The distal end 16 of device 10 terminates in an opening 17 that in certain embodiments, can be removable and/or be covered by a filter.

When a negative pressure is applied to the proximal passage 22 of the MP, air is pulled from the external environment 5 through opening 17 at the distal end 16 of device 10 and past the capsule 50 or other powder reservoir into internal chamber 26 of device 10. This air is then further pulled through an opening 32 within wall 30 of the PFD housing and into internal chamber 24 of the PFD. A portion of the air entering the chamber 24 via chamber opening 32 flows directly towards the proximal opening 11, forming a primary airflow. Additionally, the low pressure area at the distal end of internal chamber 24 creates a secondary airflow directed towards this distal end region of internal chamber 24. The decreasing cross-sectional area of chamber 24 in the distal direction causes a burst of secondary airflow which enters the pierced capsule and scours the surface of powder in the capsule, entraining a small portion of powder before rejoining the primary airflow traveling proximally towards opening 11 for inhalation by the user. An opening 40 in the housing wall 20 of the MP opens into passage 22 provides a passageway between the proximal passage 22 and the external environment 5.

Figure 5A:
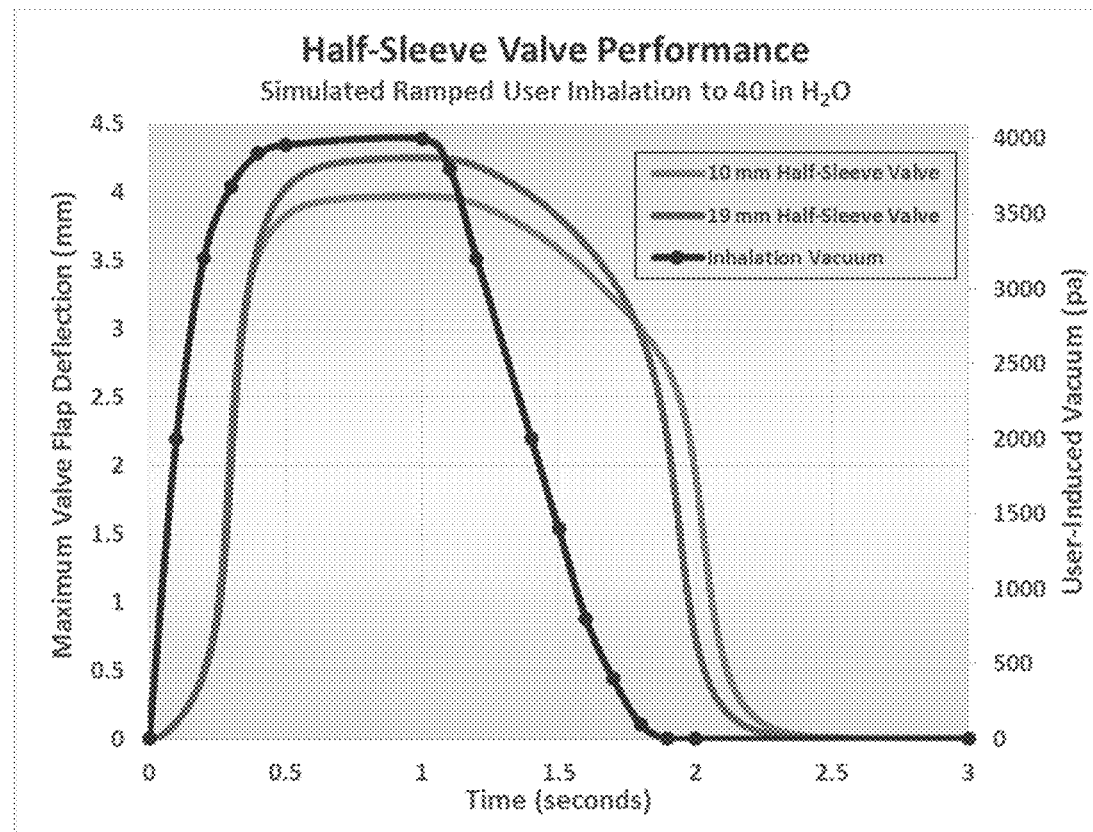
FIG. 5A is a graph showing simulated user inhalation values and valve flap deflections over time.
Figure 5B:
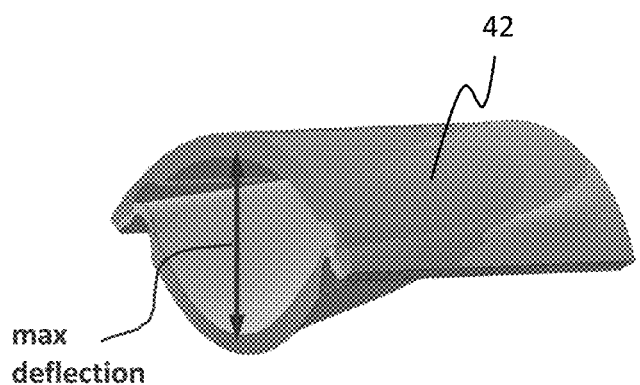
FIG. 5B is a diagram showing the valve flap deflection.

Device 10 can be used to inhale a dry powder formulation that is positioned directly into a powder reservoir chamber, or that is contained within a capsule or other separate packaging that can be placed within device 10. As contemplated herein, a single inhalation by a user can contain at least two distinct phases, where the first and second inhalation phases have different resistances to airflow. The first phase relates to an initial draw of dry powder from the reservoir or capsule primarily into the MP and mouth of the user, while the second phase relates to delivery of the airborne powder into the lungs. Preferably, the first and second inhalation phases occur within a single, continuous inhaled breath.

In one embodiment, the first inhalation phase flow resistance may operate at a negative pressure of between 35 and 55 cm $H_2O$, while the second inhalation phase flow resistance may operate at a negative pressure of between 25 and 30 cm $H_2O$. In another embodiment, the negative pressure generated during second inhalation phase may drop between 5 and 15 cm $H_2O$ as compared to the negative pressure generated during the first inhalation phase. As contemplated herein, the inhalation flow rate during the second inhalation phase remains a high enough value to maintain particle flight in the aerosol while also keeping the inhalation flow rate low enough to prevent particle impaction in the upper respiratory tract and provide advantageous delivery to the lungs.

In another embodiment, one can define flow resistance R as a function of flow rate Q and pressure drop ΔP as follows:

$$R = \frac{\sqrt{\Delta P}}{Q}$$

such that first inhalation phase flow resistance may fall in the range between approximately 0.60 and 0.75 SQRT(cm $H_2O$)/(l/min), and inhalation phase second flow resistance may fall in the range between approximately 0.1 and 0.2 SQRT(cm $H_{20}$)/(l/min).

However, it should be appreciated that there is no limitation to the timing, or length of time, of each phase of inhalation, and they may alternatively be discontinuous, as would be understood by those skilled in the art. By lowering the airflow resistance in the second phase, the same vacuum pull or draw created by the user during inhalation increases the velocity of airborne powder particles within the mouthpiece and mouth of the user, thereby permitting the airborne particles to rush down into the lungs. Thus, by replicating this two-part or two-phase movement with a dry powder inhaler allows users to experience the inhalation sensation of smoking a conventional cigarette.

Accordingly, in one embodiment, the opening 40 (or CA) can be closed or sealed by the user's finger during the first phase or portion of inhalation, such that when a user pulls a vacuum on the MP opening 11, air from the exterior environment 5 can only enter device 10 via opening 17 at the distal end of device 10. The level of resistance during this first phase is high enough to create the primary and secondary airflow paths within the PFD having enough energy to pick up powder and bring forward to passage 22 within the MP. Then, to initiate the second inhalation phase, the user uncovers the opening 40 by removing their finger, thereby introducing an influx of air at a lower resistance into passage 22. With the resistance lowered, the velocity of airflow through the MP and user's mouth momentarily increases, such that the airborne powder particles previously drawn into the MP during the first phase are quickly drawn deep into the lungs, instead of settling in the MP and user's mouth.

In another embodiment, opening 40 may further include a valve for opening and closing opening 40 to the flow of air from the external environment. For example, as shown in FIGS. 2A, 2B, 3A and 3B a uni-directional, bi-stable valve 42 is mounted on or connected to the opening 40 so that valve 42 is substantially closed at the beginning of inhalation and into the first phase of inhalation. In its closed state, as shown in FIGS. 2A and 3A, the outer surface of valve 42 follows the cylindrical shape of the device housing wall 20 so that the overall shape and feel of the device approximates the shape of a conventional cigarette. When the vacuum generating the flow of air within device 10 reaches a threshold negative pressure value, valve 42 snaps open to its open state as shown in FIGS. 2B and 3B, to allow for air to flow through the MP at a lower resistance, and consequently at a higher velocity, during the second inhalation phase as shown in FIG. 3C. For example, in one embodiment, the threshold negative pressure value may be between 35 and 55 cm $H_2O$. Once the inhalation effort drops off to a value substantially lower than threshold value, the valve 42 returns again to its closed state. As shown in FIG. 3B, when the valve 42 is open, the bottom of the valve, or valve flap, recesses into the proximal passage 22, at least partially blocking airflow between the PFD chamber 24 and passage 22. In certain embodiments, a mesh approximating the shape of the device housing is mounted over the valve 42 to protect the flexible element from damage.

With reference to FIGS. 4A and 4B, the valve 42 can be made from an elastomeric material, such as silicone rubber. The force and time required to open the valve is controlled by the durometer, thickness and/or any other nonlinear aspects of the valve material. The valve can be manufactured using any process known in the art, such as injection or compression molding. A reduced thickness region 44 can be molded into the valve for increasing flexibility of the valve to induce proper snap-through behavior on the onset of the threshold and/or differential pressure. The arc, composition, durometer and geometry of the valve can be altered to create the desired valve function, threshold and recess characteristics to achieve the timing and amount of lowered airflow resistance. For example, the graph in FIG. 5A shows a simulated user inhalation profile over the course of three seconds for a 10 mm (axial length) half-sleeve valve and the 19 mm (axial length) half-sleeve valve. By 0.3 seconds, the user-induced vacuum rises to 3500 pa, or approximately 35 cm $H_2O$, at the lower end of the opening threshold pressure. By 0.5 seconds, the user-induced vacuum jumps to almost 4,000 pa, which opens both the 10 mm half-sleeve valve and the 19 mm half-sleeve valve to just about their maximum deflections as shown in FIG. 5B. The opening delay is almost identical between the 10 mm and 19 mm half-sleeve valves. From about 0.5 seconds to 1 second, the deflection and user-induced vacuum remain at a maximum. After about 1 second, as the user inhalation vacuum starts to taper off, the valve starts to close. The difference in maximum opening deflection is insignificant in the context of flow resistance. The slight difference in closing hysteresis between the 10 mm and 19 mm half-sleeve valves is expected, based on the geometrical differences in the valve structures.

Figure 7A:
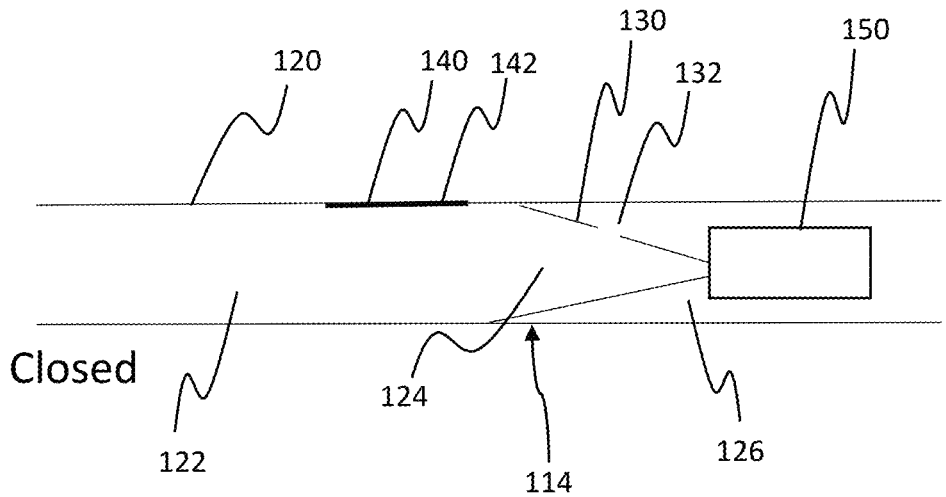
FIGS. 7A and 7B are cross-sectional views of a dry powder inhaler according to an exemplary embodiment of the invention.
Figure 7B:
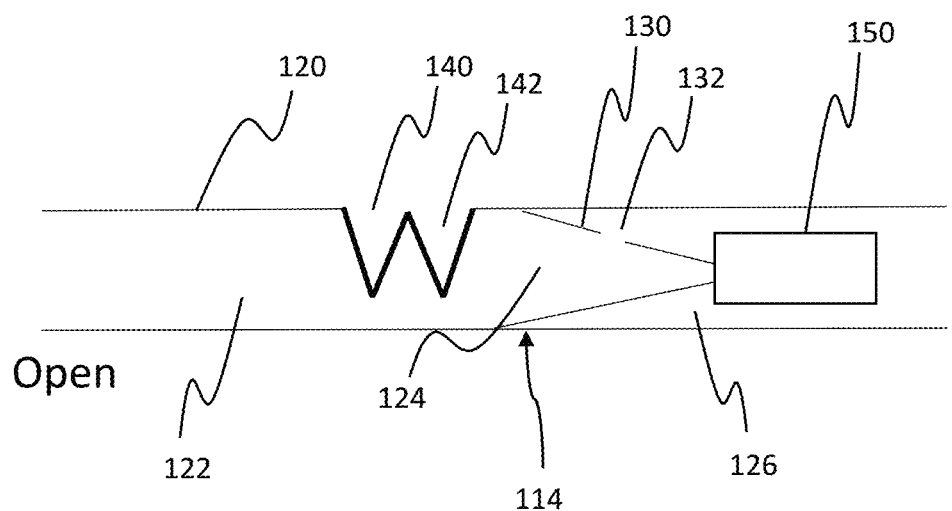

An alternative valve embodiment is shown in FIGS. 6A-6C, 7A and 7B. The pressure actuated valve 142 is substantially disc shaped and has at least one slit 144, or as shown, a plurality of slits that intersect at the center of the valve 142. The opening 140 in the device housing wall 120 is sealed by the pressure actuated valve 142. The valve 142 can be constructed of a Mooney-Rivlin hyperelastic, or an equivalent approximately 35 Shore A material. In another embodiment, the material may be a silicone rubber or similar hyperelastic material having a Shore A durometer value between 5 and 80 and preferably between 10 and 40. During use, the valve 142 is substantially closed at the beginning of inhalation and is held closed during the first inhalation phase, such as for a period of less than one second. In this closed position, the outer surface of the valve may also have a profile that is close to the surface of the device housing wall 120 so that the overall shape and feel of the dry powder inhaler comes close to approximating the shape of a conventional cigarette, if desired. A capsule or reservoir 150 is positioned within the distal passage 126 of the device, in fluid communication with the PFD chamber 124 and adjacent to a portion of the PFD interior walls 130. The valve 142 snaps into an open position as shown in FIGS. 6C and 7B, to allow for lower resistance in the system once a threshold negative pressure is reached within the MP internal passage 122. The valve 142 then returns to its closed state after passing the threshold pressure value as passage 122 returns to atmospheric pressure. Further, as shown in FIG. 7B, when the valve 142 is open, the bottom edges or flaps of the valve recess into passage 122, at least partially blocking airflow between the chamber 124 and passage 122. This valve embodiment may provide a larger airflow cross-section when open, for a faster reduction of airflow resistance. This effect, similar to previous embodiments, creates a bi-stable characteristic of the dry powder inhaler, providing a two-part movement sensation of smoking a cigarette within a single inhalation.

Figures 8A, 8B:
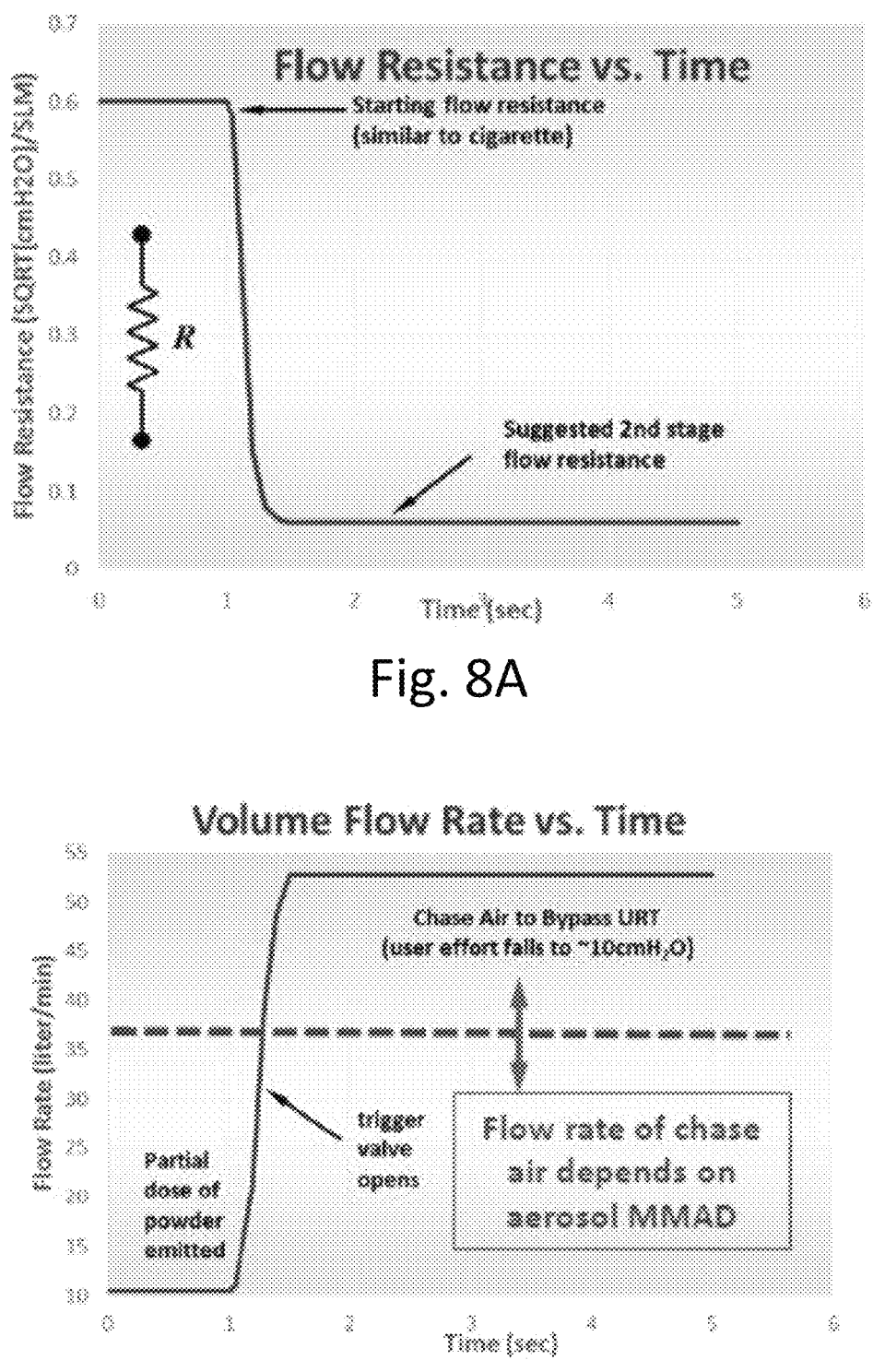

While the valves depicted herein are mechanical valves actuated by negative pressure generated by an inhalation airflow, the present invention is not limited to such designs. For example, alternative designs may include other mechanical threshold valves, electronic valves, or any other valve understood by those skilled in the art. Further, the position, shape and size of the valve, and corresponding opening in which the valve is positioned can vary, as alternate configurations can allow air to be introduced into the mouthpiece from the external environment. For example, inhaler device designs can approximate the flow resistance and volume flow rate models shown in the graphs of FIGS. 8A and 8B. The user pulls at 20-40 cm $H_2O$ for about one second, similar to drag on a cigarette. The powder particles are fluidized and deagglomerated, and enter the device mouthpiece, as well as the user's mouth and the upper respiratory tract (URT). After about one second, or in some embodiments after about 0.1 to 0.5 seconds, the second phase flow path opens via the opening valve, and chase air is delivered at a much lower flow resistance. The higher flow rate increases airborne particle velocity, and therefore takes the aerosol comfortably beyond the upper respiratory tract to the lungs.

Without being limited to any particular theory, an important aspect of the device and system is the delay between the onset of a threshold negative pressure value and the opening of valve 42. During this delay, a predetermined or approximate amount of powder is fluidized and deagglomerated through the PFD. Time values for this delay may range from 0 to 0.5 seconds, and preferably between 0.1 and 0.25 seconds. In some embodiments, the delay may be inversely related to peak negative pressure generated by the user, but this relationship may counterbalance the powder uptake from the PFD, which is also positively related to peak negative pressure generated by the user.

At the instant that valve 42 opens, it is expected that the negative pressure within the proximal region of the internal passage will fall to a lower value. This drop in negative pressure also serves to inhibit aerosol production through the PFD. Therefore another important aspect of the system and device is the requirement for significant material hysteresis, such that valve 42 stays open while negative pressure within the proximal region of the internal passage falls to a value that may be below the threshold negative pressure value.

In another aspect, a method for delivering a dry powder composition into the lungs of a user is described. As contemplated herein, the method includes the steps of inserting a dry powder composition into an inhaler, generating a negative pressure within the inhaler via an inhalation by a user to create a first airflow pattern within the inhaler at a first airflow resistance, such that at least a portion of the dry powder composition becomes airborne within the inhaler, and generating a second airflow pattern within the inhaler having a second airflow resistance that is lower than the first airflow resistance, such that the airborne dry powder is pulled by the negative pressure into the user's lungs during the inhalation. The methods may be performed using any embodiments of the dry powder inhalers described and contemplated herein. For example, in one embodiment, the step of generating the second airflow pattern is automated by the inhaler via opening and closing of a valve associated with the proximal region opening within the device external housing. Accordingly, generating the second airflow pattern may occur when a threshold negative pressure value is reached within the internal passage of the inhaler. In another embodiment, the first airflow pattern is at least partially blocked by the generation of the second airflow pattern, via one or more flaps of the valve recessing into the internal passage of the inhaler.

With reference now to embodiments of valve designs, the valves disclosed herein are generally of the type for regulating the movement of gases, matter in a gaseous state, or materials in a gaseous-like state, including but not limited to air, aerosolized substances such as powders or liquids, nitrogen, helium, carbon dioxide, water vapor, natural gas, hydrogen, oxygen, propane, and other various natural and manufactured chemical gases.

Figure 9A:
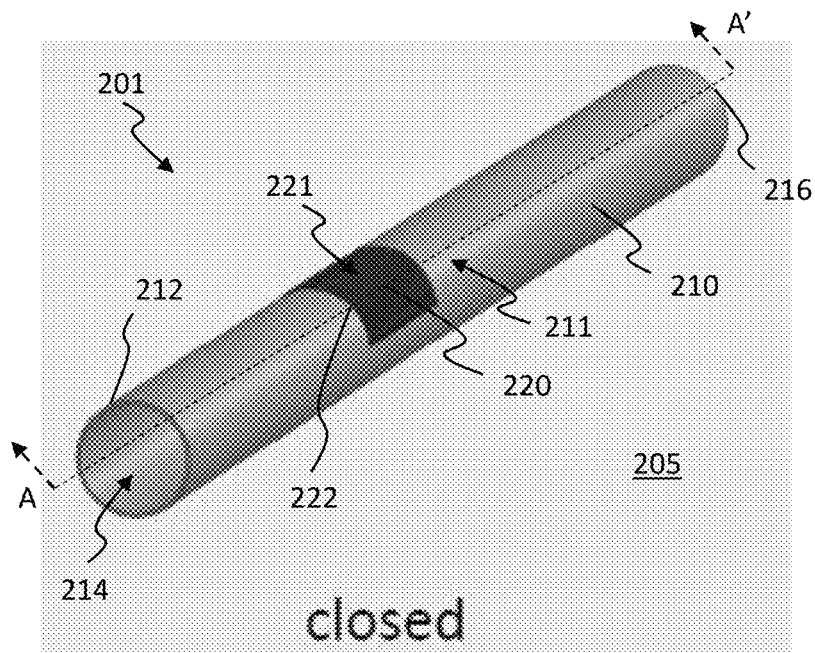
FIGS. 9A and 9B are perspective views of a valve positioned in a conduit housing, according to an exemplary embodiment of the invention.
Figure 9B:
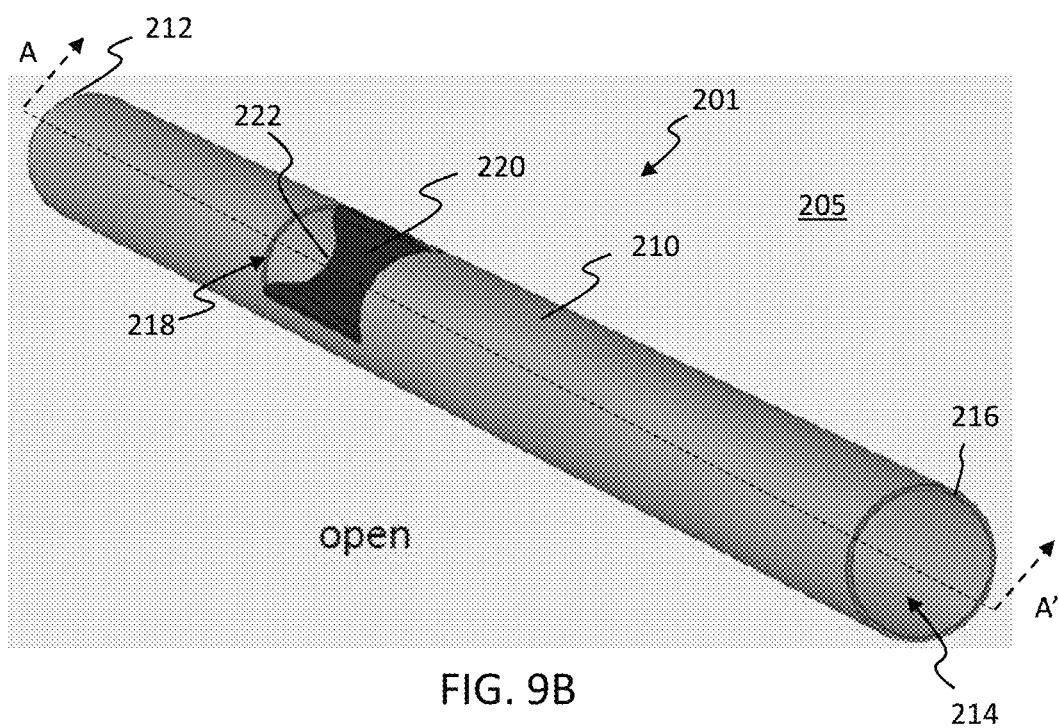

Now with reference to an embodiment 201 of the invention shown in FIGS. 9A and 9B, the valve 201 may be positioned within a wall of a conduit, such as a cylindrical or generally tubular sidewall 210 defining a tubular lumen 214 that extends between a first opening 212 and a second opening 216. In alternative embodiments, the sidewall 210 can have a number of geometrical structures, such as triangular, square, pentagonal, trapezoidal, or approximating any type of polygon. In some alternative embodiments, the lumen 214 may be one shape, for example, generally circular, while the outer surface of the sidewall is another shape, such as square or another polygon or trapezoid-like shape. In certain embodiments, the sidewall 210 and lumen 214 are elongate, while changing their geometric profile and size along their length. As shown in the exemplary embodiment, the first opening 212 and the second opening 216 are circular openings that open to air in the surrounding environment 205. In preferred embodiments, the first 212 and second 216 openings are generally the same shape and size as the lumen 214, however, they can be different shapes and sizes as desired.

As shown specifically in FIG. 9B, a sidewall opening 218 is formed in the sidewall 210 between the first opening 212 and the second opening 216, providing fluid communication between the lumen 214 and the surrounding environment 205. Depending on its application, the valve can be integrated into a larger system such that any of the first 212 and second 216 openings, or the sidewall opening 218, leads to a particular system pathway, such as a secondary tube, a container, or the external environment 205. Examples of these types of configurations are shown in later embodiments. The sidewall opening 218 in FIG. 9B is substantially rectangular in shape when viewed from the top of device 201, and is covered by a flexible elastomeric member 220 also having a generally rectangular profile from a top view perspective. The elastomeric member 220 is housed within sidewall opening 218 such that the outer surface 221 of the elastomeric member 220 substantially matches the outer surface 211 of the sidewall 210. This creates an aesthetically pleasing continuity in the transition between the sidewall outer surface 211 and the valve outer surface 221, if desired. In the case of the exemplary embodiment, the elastomeric member 220 is housed to curve as it sets within its housing, so that the curvature of the surface 221 of the elastomeric member 220 is substantially follows the same cylindrical curvature or profile of the surface 211 of the sidewall 220. The elastomeric member 220 can be attached to cover the sidewall opening 218 using methods known in the art, such as overmolding or other injection molding techniques, a compression fitting that mates opposing shaft sections of the sidewall 210 at edges of the member, or use of an adhesive around edges of the sidewall opening 218. In alternative embodiments, the sidewall opening 218 profile and the elastomeric member 220 are non-rectangular, and take-on a triangular, square, pentagonal, trapezoidal, or other polygonal shape, or could also be a contoured and curved shape. Depending on the geometry and contour of the outer surface 211 of the sidewall 210, the elastomeric member 220 can be flexed, molded and manipulated to set within its housing so that its surface 221 matches the profile of sidewall surface 211. For instance, if the elastomeric member is housed in a sidewall along a flat surface, it can be housed to rest in a flat configuration instead of a curved configuration. In certain embodiments, the elastomeric member 220 can be constructed of a hyperelastic material, or an equivalent approximately 35 Shore A material. In another embodiment, the elastomeric member 220 can be constructed of a silicone rubber or similar hyperelastic material having a Shore A durometer value between 5 and 80 and preferably between 10 and 40. The elastomeric member 220 can be manufactured using any process known in the art, such as injection or compression molding.

As seen with specific reference to the exemplary embodiment shown in FIG. 9B, the elastomeric member 220 is attached to the rectangular sidewall opening 18 along three of its four edges. The elastomeric member 220 is flexible, and the detached edge 222 allows portions of the member 230 to flex down at least partially into the lumen 214 when a threshold pressure differential is applied across the elastomeric member 220. As contemplated herein, at least one edge of the elastomeric member is detachable from the conduit wall. In certain embodiments, two or more edges are detachable, depending on the shape of the conduit in which the member is housed, and the shape and depth of the lumen of the conduit. The threshold pressure differential required to flex the elastomeric member 230 can be predetermined based on a number of factors, which include the arc of the member within its housing, the material composition, the durometer and the shape of the member or portions of the member, and additional factors disclosed herein.

Figure 10A:
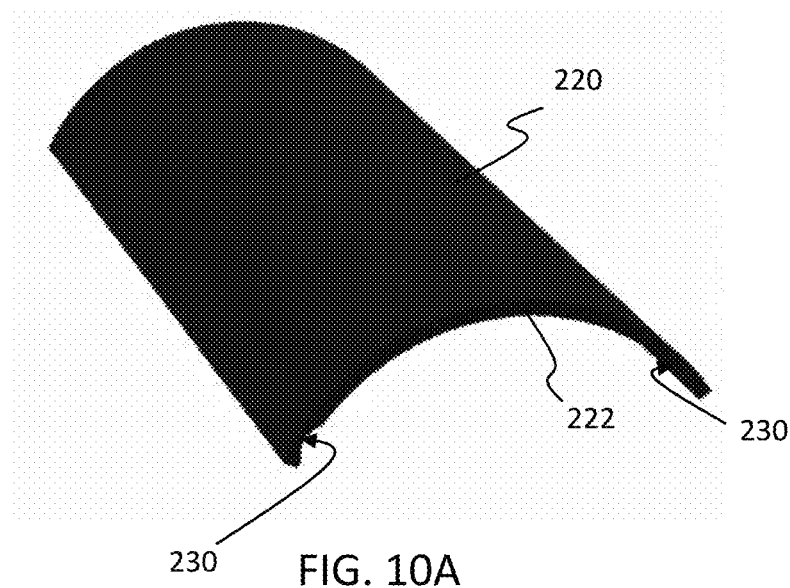
FIGS. 10A-10C show an exemplary elastomeric member component of a valve, according to an aspect of the invention.
Figure 10B:
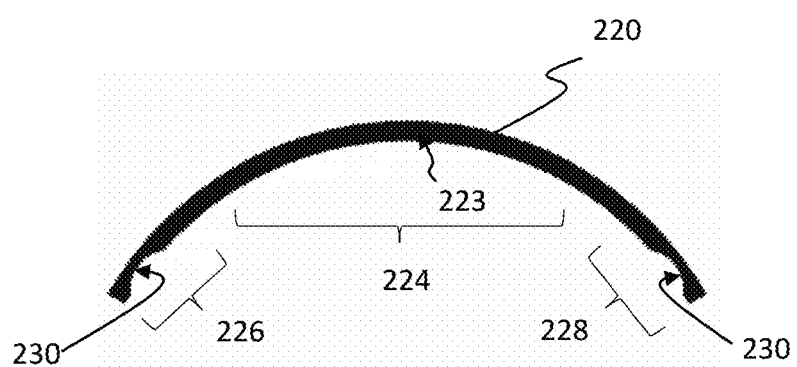
Figure 10C:
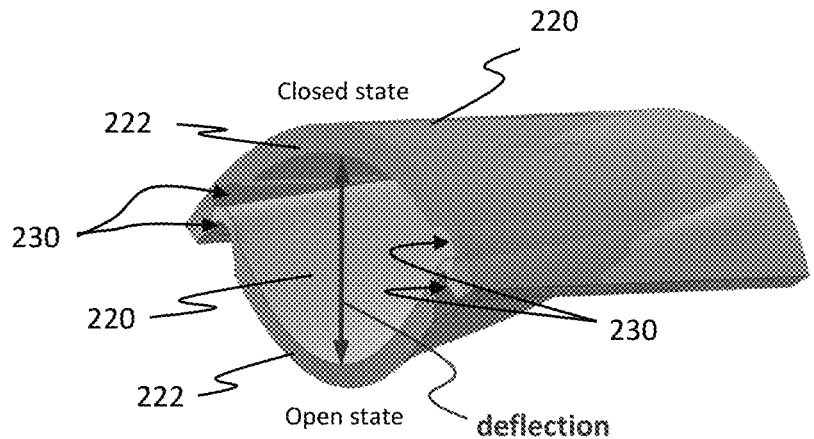

Another characteristic of the elastomeric member that influences its flexing movement is its variable thickness, as illustrated in FIGS. 10A-10C. The variable thickness at selected portions of the member 220 can be used to set a predetermined threshold pressure differential to initiate flection. Accordingly, variable thickness within at least a portion of the member may be used to initiate a bi-stable "snap-through" movement of the elastomeric member 220, so that the member 220 effectively snaps-through from its closed state to its open state without sustaining an intermediate geometry. As shown specifically in FIG. 10B, the elastomeric member 220 has a first periphery region 226 and a second periphery region 228, each at opposite sides of a central region 224 of the member 220. The thickness 230 of the member 220 at the first and second periphery regions 226, 228 is less than the thickness 223 of the member 220 at the central region 224. This reduced thickness increases flexibility of the member 220 at the peripheral regions 226, 228 to induce and reliably control the snap-through (bi-stable) behavior at the onset of the threshold differential pressure within the lumen of the associated conduit. Once opened, the valve stays in its open bi-stable state, until the pressure passes back across the threshold value. However, another important aspect of the elastomeric member flection is the requirement for significant hysteresis, such that the valve member remains temporarily open while pressure within the lumen passes back across the threshold value. Such hysteresis is similarly demonstrated in the graph of FIG. 5A. In certain embodiments, once opened at threshold negative pressure, it would be advantageous for the valve to remain in its bi-stable open state for at least one second, and after that the negative pressure within the proximal region of the internal passage reaches a value as low as 8 cm $H_2O$.

With reference back to FIGS. 10A-10C, the reduced thickness 230 of the member 220 at the first 226 and second 228 periphery regions can extend at least partially or fully back away from the detached edge 222 and along the sides of the member 220, forming channels in the member 220 that are substantially parallel to each other. In preferred embodiments, and as shown in the exemplary embodiment, the channels and reduced thickness are formed in a bottom surface of the elastomeric member, so that they do not interfere with the aesthetic value attributes discussed above. Depending on the desired flection characteristics and the geometry of the member and sidewall openings, the channels can be designed to taper off in thickness, and either diverge or converge as they extend away from the detached edge 222. As illustrated in FIG. 10C, the variable thickness and channels in the member 220 described herein facilitates the bi-stable nature of the valve, inducing the onset of the snap-through movement. As a result, the valve effectively has two binary states of "open" and "closed", with the inability to sustain an intermediate geometry. This is beneficial for a number of applications, since a bi-stable valve movement in a valve that automatically actuates in response to pressure allows more certainty and predictability in systems and devices utilizing the valve.

Figure 11A:
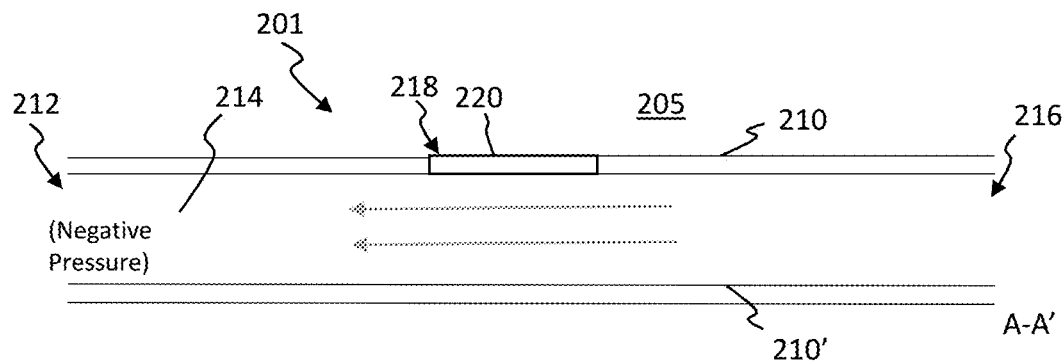
FIGS. 11A-11C are cross-sectional views of an exemplary valve similar to that shown in FIGS. 9A and 9B taken across cross section A-A'.
Figure 11B:
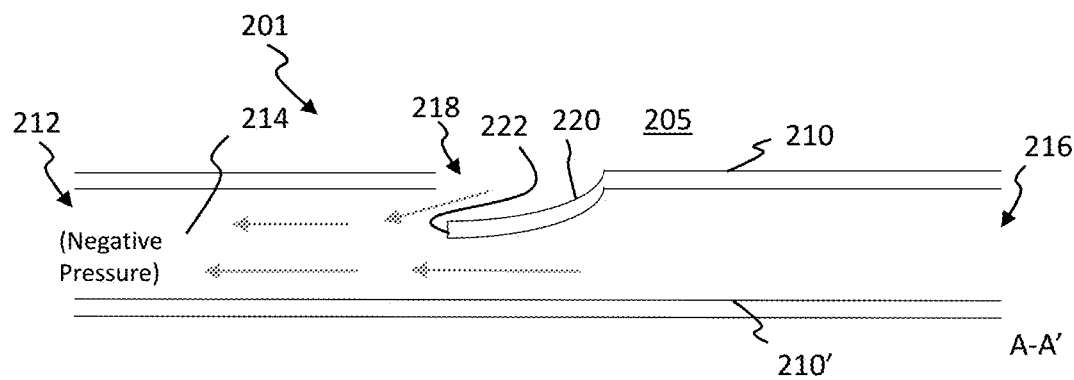
Figure 11C:
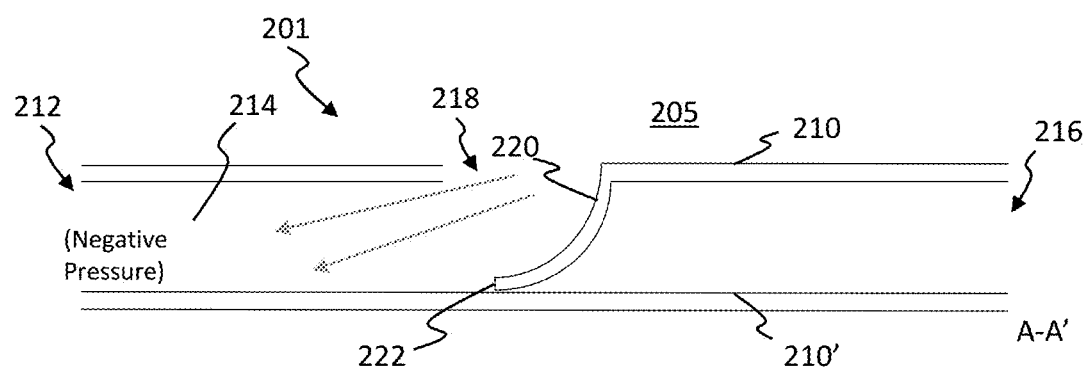
Figure 12A:
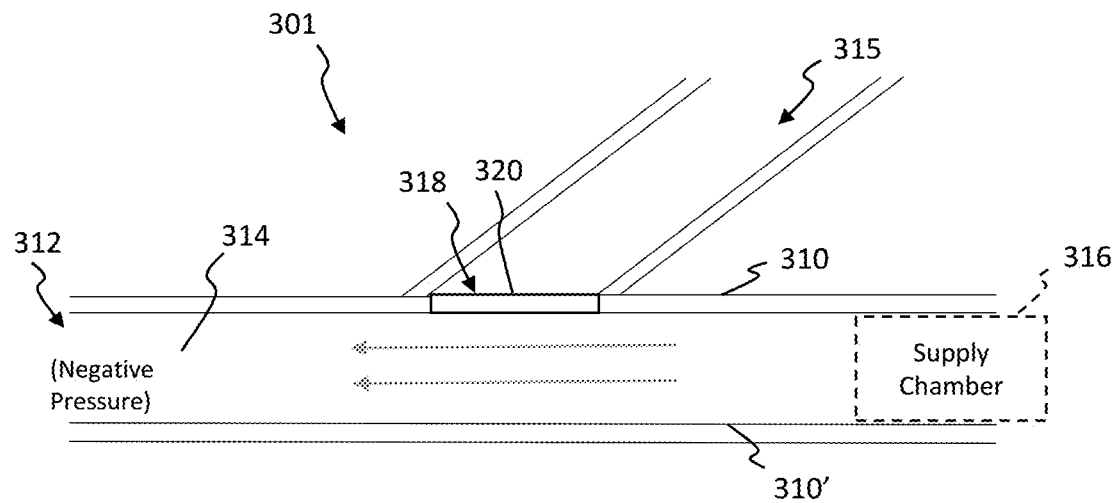
FIGS. 12A and 12B are cross-sectional views of an exemplary valve having a second lumen and a supply chamber according to an exemplary embodiment of the invention.
Figure 12B:
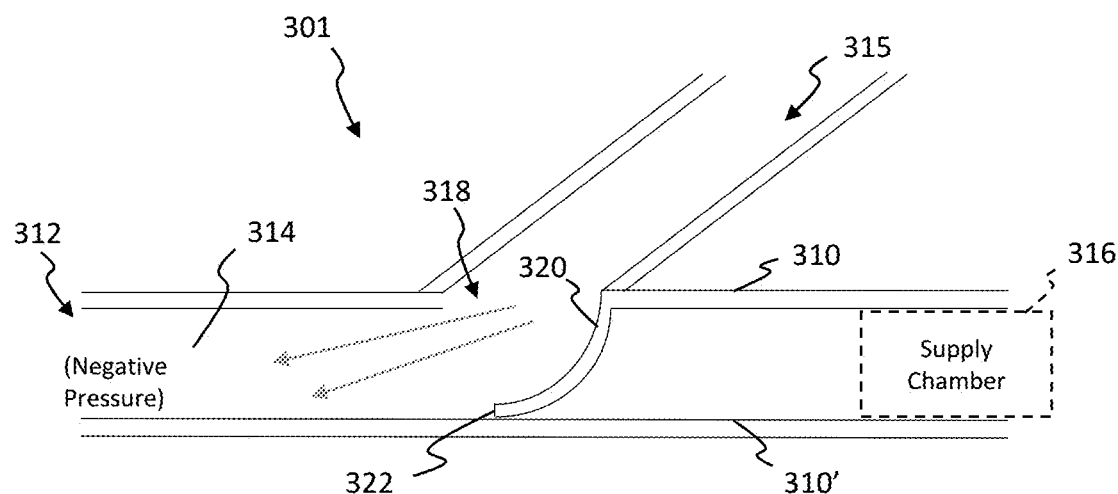
Figure 13A:
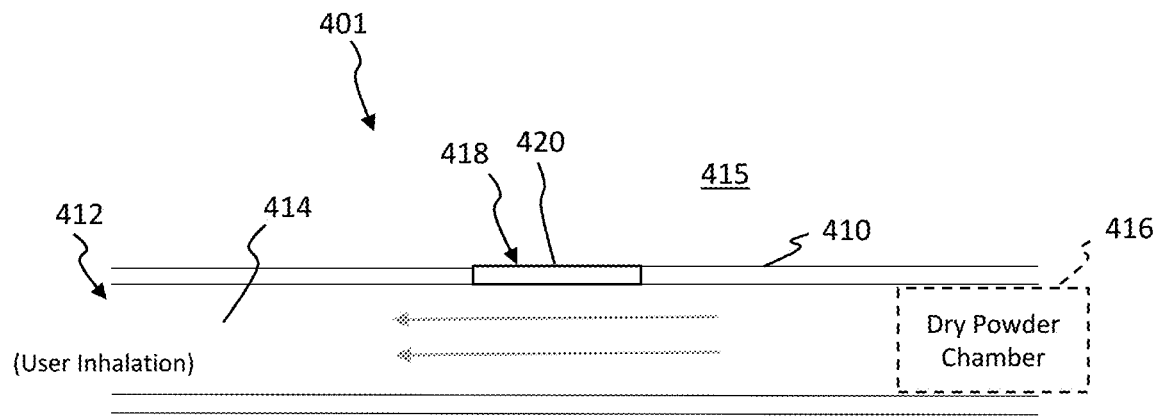
FIGS. 13A and 13B are cross-sectional views of a dry powder inhaler incorporating an exemplary embodiment of the valve into its dry powder inhaler design.
Figure 13B:
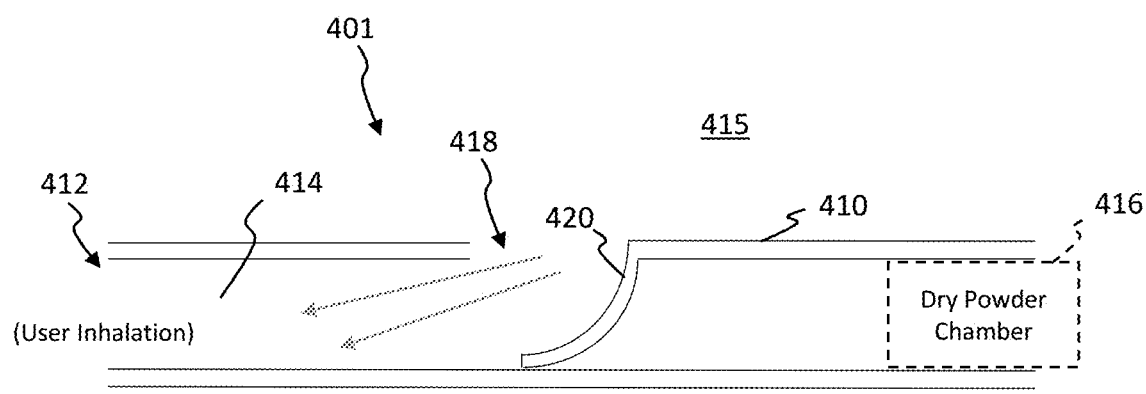

Now with reference to FIGS. 11A-11C, various operational states of the valve are shown according to an exemplary embodiment. In FIG. 11A, a negative pressure is applied at the first opening 212. Since the elastomeric member 220 does not open until the threshold pressure is reached, it remains in a closed state, keeping the sidewall opening 220 closed, and blocking the flow of gas (is this case air) between the external environment 205 and the lumen 214. Thus, the negative pressure at the first opening 212 draws air entirely from the second opening, which for example could be a gas supply container or a powder chamber for supplying an aerosolized gaseous flow. FIG. 11B shows the elastomeric member 220 flexing downward partially into the lumen of the conduit. In this embodiment, the member 220 flexes down to its open state, and is designed to partially block the lumen 214 and allowing the negative pressure to draw air from a mixture of the second opening 216 and the external environment 205. Depending on the desired performance of the valve and the desired mixture, the member 220 may be designed to block a small portion of the lumen 214, substantially half of the lumen 214, or almost all of the lumen 214. Meanwhile, FIG. 11C shows the elastomeric member 220 in a fully open state. Here, the member 220 snaps-through to a position that either contacts or comes very close to contacting an inner wall 210' of the sidewall 210, extending fully across the lumen 214. In the fully open state, substantially all flow between the second opening 216 and the first opening 212 is restricted, since the lumen 214 is effectively closed by the elastomeric member 220. Consequently, the negative pressure draws in air exclusively from the external environment. For both embodiments, as mentioned above, even though the pressure returns within the lumen 214 as the elastomeric member 220 opens, hysteresis delays the closing of the member 220, and allows the continuation of the open state for a short period of time (e.g. a fraction of a second, or between 1 and 2 seconds).

The advantages of the pressure actuated elastomeric valve are apparent. With such a simple geometry, the elastomeric member is easy to manufacture. When exposed to a visible surface, the elastomeric member is able integrate itself with the contours of its associated device, thus maintaining a high aesthetic value for the valve and the device. Seating for the elastomeric member will not add significant housing bulk since the elastomeric member geometry approximates the wall of its associated lumen, minimizing impedance with flow pathways. Further, the design is favorable to durable performance and reliable actuation in response to a pressure generated by a gas or gas-like medium. In addition, the bi-stable movement and hysteresis of the flection between open and closed states are of significant advantage in many industries and for many applications, further ensuring a high degree of predictability in valve performance.

As mentioned above, depending on its application, the valve can be integrated into a larger system, such that any of the first 212 and second 216 openings, or the sidewall opening 218 from earlier embodiments leads to a particular system pathway, such as a secondary tube, a container, or the external environment 205. With reference now to FIGS. 12A and 12B, an exemplary embodiment of the valve 301 utilizes a supply chamber 316 opposite the first opening 312 of the first lumen 314, and a second lumen 315 connected to the first lumen 314 via the sidewall opening 318. The elastomeric member 320 essentially regulates the flow of gases between the first opening 312, the second lumen 315 and the supply chamber 316. As would be apparent to those having ordinary skill in the art, the supply chamber 316 could be located in communication with the second lumen 315 instead of the first lumen 314. In the exemplary embodiment, until the pressure differential crosses the threshold value for opening the elastomeric member 320, it will stay closed, effectively sealing-off gaseous flow between the second lumen 315 and the first lumen 314 (and first opening 312). Thus, while the valve is closed, the flow of gas will come entirely from the supply chamber 316. However, if the pressure differential crosses the threshold value, the member 320 will snap-through to its open state, and the at least one detached edge 322 will flex downward to the inside surface 310' of the sidewall 310. The open state may at least partially block the flow of gases between the supply chamber 316 and the first opening 312, while opening to flow between the second lumen 315, the first lumen 314 and the first opening 312. Subsequently a pressure return across the threshold value allows the member to snap-through back to a closed state. Alternative embodiments could configure the open state to a partially blocking configuration as described in previous embodiments, allowing a mixture of flow from both the second lumen and the supply chamber. In still other embodiments, a buildup of pressure, such as via the introduction of air or other gasses, in second lumen 315 may serve to actuate valve 320 and allow for the subsequent release of the air and gasses into lumen 314. After sufficient reduction of pressure in lumen 315, the valve 320 snaps back to its original state. As such, valve 320 may function as a venting or purge valve.

The valve mechanism disclosed herein has potential benefits and advantages across many industries. By way of just one example, the valve mechanism can be used to facilitate the inhalation of a dry powder formulation in a dry powder inhaler device. Inhalation of nicotine-based powder formulations has become an effective and popular way to deliver nicotine to the bloodstream while reducing the hazardous effects of smoking, such as those associated with unpleasant odors and second hand smoke. For example, dry powder inhalers allow users to inhale nicotine powder from the device for delivery to the lungs and absorption into the bloodstream.

As shown in the exemplary embodiment of a dry powder inhaler 401 in FIGS. 13A and 13B, the dry powder is stored in a dry powder chamber 416 situated at one end of the lumen 414. Alternatively, it can be contained within a capsule or other separate packaging that can be placed within the first lumen 414. As contemplated herein, a single inhalation at the first opening 412 by a user can contain at least two distinct phases, where the first and second inhalation phases have different resistances to airflow. The first phase relates to an initial draw of dry powder from the dry powder chamber 416 or capsule primarily into the mouth of the user, while the second phase relates to delivery of the airborne powder into the lungs. Preferably, the first and second inhalation phases occur within a single, continuous inhaled breath. In the first phase, the elastomeric member 420 is in a closed state, and the applied vacuum disturbs the powder in the dry powder chamber 416, bringing it out of the chamber 416 and into the lumen 414 while the pressure in the lumen approaches the threshold differential. The second phase initiates as the threshold pressure is crossed, and provides chase air through the sidewall opening 418 when the elastomeric member 420 opens, providing a sudden rush of air introduced into the lumen 414 from the external environment 415. This chase air carries the aerosolized powder past the user's mouth and upper respiratory tract to the user's lungs. As pressure returns towards the end of inhalation, the member snaps-through back to a closed state. In alternative embodiments, the member is configured to open to a partially blocking configuration as described in previous embodiments, allowing a mixture of flow from both the external environment and the dry powder chamber. Advantageously, a single inhalation by a user can contain two phase inhalation movement, for delivering airborne powder into the lungs, all with a single, smooth and continuous inhaled breath.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for inhalation of a dry powder composition, comprising:
   an external housing comprising a housing wall and having a proximal end, a distal end and a length therebetween, wherein the housing defines an internal passage having proximal, intermediate and distal regions along the housing length;
   a proximal end opening, a distal end opening, and proximal region opening extending through the housing wall, each opening being in connection with the internal passage;
   a dry powder compartment within the distal region of the internal passage;
   a powder fluidization and deagglomeration apparatus within the intermediate region of the internal passage; and
   a valve disposed at the proximal region opening, the valve having a closed position and an open position,
      wherein in the closed position a first airflow path extends from the distal end opening to the proximal end opening having a first airflow resistance, and in the open position, a second airflow path is open having a second airflow resistance that is lower than the first airflow resistance and the first airflow path is at least partially blocked by the valve.

2. The device of claim 1, wherein the valve is configured to open responsive to a threshold negative pressure within the proximal region of the internal passage.

3. The device of claim 1, wherein the valve comprises a flexible component attached to only a portion of a proximal region opening perimeter.

4. The device of claim 3, wherein the portion of the flexible component detached from the proximal region opening perimeter forms a flap that separates from the proximal region opening perimeter and at least partially recesses into the internal passage when a threshold negative pressure value is reached within the internal passage.

5. The device of claim 1, wherein the valve comprises a flexible component having at least one slit to form at least one valve flap.

6. The device of claim 5, wherein the at least one valve flap at least partially recesses into the internal passage when a threshold negative pressure value is reached within the internal passage.

7. The device of claim 2, wherein the valve is a mechanical valve.

8. The device of claim 1, wherein the dry powder compartment is a disposable capsule positioned within the distal region of the internal passage.

9. The device of claim 1, wherein the dry powder compartment is a reservoir.

10. The device of claim 1, wherein the powder fluidization and deagglomeration apparatus is in fluid communication with the dry powder compartment.

11. The device of claim 1, wherein the powder fluidization and deagglomeration apparatus is detachable from the device housing.

12. The device of claim 1, wherein the powder fluidization and deagglomeration apparatus is integrated with the device housing.

13. The device of claim 1, wherein the external housing is substantially cylindrical along its length.

14. The device of claim 1, wherein the valve has a profile that is substantially the same as the profile of the external housing adjacent the proximal region opening.

* * * * *